(12) United States Patent
Wu et al.

(10) Patent No.: US 8,399,691 B2
(45) Date of Patent: Mar. 19, 2013

(54) METHOD FOR RESOLUTION OF A MIXTURE OF PINOCEMBRIN OPTICAL ISOMERS, ESPECIALLY A PINOCEMBRIN RACEMATE

(75) Inventors: Song Wu, Beijing (CN); Guanhua Du, Beijing (CN); Yue Yuan, Beijing (CN); Qingyun Yang, Beijing (CN); Mei Gao, Beijing (CN); Yan Qi, Beijing (CN); Yuanfeng Tong, Beijing (CN); Yuehua Wang, Beijing (CN)

(73) Assignees: CSPC Zhongqi Pharmaceutical Technology (Shijiazhuang) Co. Ltd. (CN); Institute of Materia Medica, Chinese Academy of Medical Sciences (CN)

( * ) Notice: Subject to any disclaimer, the term of this patent is extended or adjusted under 35 U.S.C. 154(b) by 316 days.

(21) Appl. No.: 12/741,143

(22) PCT Filed: Nov. 7, 2008

(86) PCT No.: PCT/CN2008/072983
§ 371 (c)(1),
(2), (4) Date: May 3, 2010

(87) PCT Pub. No.: WO2009/067904
PCT Pub. Date: Jun. 4, 2009

(65) Prior Publication Data
US 2010/0261916 A1    Oct. 14, 2010

(30) Foreign Application Priority Data
Nov. 8, 2007 (CN) .......................... 2007 1 0177016

(51) Int. Cl.
*C07D 311/32* (2006.01)
(52) U.S. Cl. ...................................... 549/403
(58) Field of Classification Search .................... 549/403
See application file for complete search history.

(56) References Cited

FOREIGN PATENT DOCUMENTS
EP          1389606 A1     2/2004
JP          2005-176758 A  7/2005

OTHER PUBLICATIONS

Asztemborska, M., et al., "Separation of some chiral flavanones by micellar electrokinetic chromatography", *Electrophoresis*, 24(15), (2003), 2527-2531.

Caccamese, S., et al., "High-performance liquid chromatographic separation and chiroptical properties of the enantiomers of naringenin and other flavanones", *Journal of Chromatography A*, 1076(1-2), (2005), 155-162.

Ding, Y., et al., "Theoretical Calculation of Electronic Circular Dichrosim of the Rotationally Restricted 3,8"-Biflavonoid Morelloflavone", *The Journal of Organic Chemistry*, 72(24), (2007), 9010-9017.

Duan, Y.-B., et al., "Synthesis and antimicrobial activity of pinocembrin and its derivatives", *Chinese Journal of Medicinal Chemistry*, 16(6) , (2006), 342-346.

Holder, S., et al., "Comparative molecular field analysis of flavonoid inhibitors of the PIM-1 kinase", *Bioorganic & Medicinal Chemistry*, 15(19), (2007), 6463-6473.

Lepri, L., et al., "Reversed-Phase Planar Chromatography of Racemic Flavanones", *Journal of Liquid Chromatography & Related Technologies*, 22(1), (1999), 105-118.

"European Application Serial No. 08854402,8, Supplementary European Search Report mailed Oct. 28, 2011", 8 pgs.

Eliel, E. L., "7-3. Chemical Separation of Enantiomers via Diastereomers", In: *Stereochemistry of Organic Compounds*, (1994), 322-381.

Krause, M., et al., "Direct enantiomeric separation of racemic flavanones by high-performance liquid chromatography using cellulose triacetate as a chiral stationary phase", *Journal of Chromatography*, 441, (1988), 417-422.

Yuan, Y., et al., "Synthesis and enantiomeric resolution of (±) pinocembrin", *Journal of Asian Natural Products Research*, 10(10), (2008), 999-1002.

"International Application Serial No. PCT/CN2008/072983, International Search Report mailed Feb. 12, 2009", 8 pgs.

Holder, S., et al., "Characterization of a potent and selective small-molecule inhibitor of the PIM1 kinase", *Mol. Cancer Ther.*, 6(1), (2007), 163-172.

*Primary Examiner* — Bernard Dentz
(74) *Attorney, Agent, or Firm* — Schwegman Lundberg & Woessner, P.A.

(57) ABSTRACT

The present invention relates to a method for resolution of a mixture of pinocembrin optical isomers, in particular a pinocembrin racemate, using a chiral primary amine or a chiral sulfinamide. The present invention also relates to a (R)-(+)-pinocembrin obtained by the method.

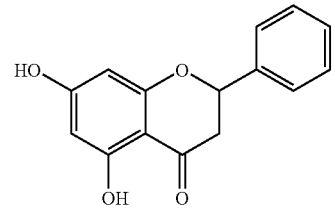

13 Claims, No Drawings

METHOD FOR RESOLUTION OF A MIXTURE OF PINOCEMBRIN OPTICAL ISOMERS, ESPECIALLY A PINOCEMBRIN RACEMATE

RELATED APPLICATIONS

This application is a nationalization under 35 U.S.C. 371 of PCT/CN2008/072983, filed Nov. 7, 2008 and published as WO 2009/067904 A1 on Jun. 4, 2009, which claimed priority under U.S.C. 119 to Chinese Patent Application Serial No. 200710177016.X, filed Nov. 8, 2007, which applications and publication are incorporated herein by reference in their entirety.

TECHNICAL FIELD

The present invention relates to the pharmaceutical field. Specifically, the present invention relates to a method for resolution of a mixture of pinocembrin optical isomers, especially a pinocembrin racemate, into enantiomers with single configuration.

BACKGROUND ART

Pinocembrin has a chemical name of 2,3-Dihydro-5,7-dihydroxy-2-phenyl-4H-1-benzopyran-4-one. Pinocembrin is a flavanone compound having one chiral center in its chemical structure. Natural pinocembrin has a steric structure of S-configuration and a specific rotation $[\alpha]D^{15}$ of −45.3 (c, 0.9, acetone as solvent). Pinocembrin can be separated from propolis as well as plants such as *Pinus cembra, Eucalyptus sieberi, Alnus sieboldiana* in a relatively low level. Accordingly, the complete synthesis thereof has been studied in the art and pinocembrin in form of racemate can be prepared in large scale (DUAN Yabo, et al., *Chinese Journal of Medicinal Chemistry*, 16(6): 342-346, 2006).

Pinocembrin has one chiral carbon in its molecule and thus has a pair of enantiomers i.e., (R)-pinocembrin and (S)-pinocembrin. Natural pinocembrin is (S)-pinocembrin, but its content in plants is very low and thus can not be obtained in large scale, whereas the studies on biological activities of (R)-pinocembrin are not found yet. In addition, pinocembrin has not a salt-forming acidic or basic group in its structure, so that the optical resolution of pinocembrin can not be performed by a conventional method of forming diastereomer salts. Currently, none of other methods such as crystallization, mechanical method or selective adsorption is found suitable for the resolution.

Therefore, there remains a need for a method for resolution of racemic pinocembrin to obtain a pinocembrin enantiomer with single configuration.

CONTENTS OF THE INVENTION

It was found surprisingly by the inventors that a mixture of pinocembrin optical isomers, in particular a pinocembrin racemate, can be effectively resolved by using a chiral primary amine or a chiral sulfinamide as resolving agent.

In one respect, therefore, the present invention provides a method for resolution of a mixture of pinocembrin optical isomers, in particular a pinocembrin racemate, comprising performing the resolution by using a chiral primary amine or a chiral sulfinamide as resolving agent. In one embodiment, the method comprises the following steps: (1) converting a mixture of pinocembrin optical isomers, in particular a pinocembrin racemate, into a mixture of diastereoisomer derivatives by using a chiral primary amine or a chiral sulfinamide; (2) separating and dederivatizing the pair of diastereoisomers by utilizing their different physical properties to obtain (R)-(+)-pinocembrin and (S)-(−)-pinocembrin with optical activity. Optionally, dederivatizing the separated and purified diastereoisomers comprises hydrolysis, reduction and optional purification thereof to obtain single enantiomers of pinocembrin.

In a further respect, the present invention provides a (R)-pinocembrin obtainable from racemic pinocembrin by the method of resolution according to the present invention.

SPECIFIC MODELS FOR CARRYING OUT THE INVENTION

In one embodiment, the present invention provides a method for resolution of a mixture of pinocembrin optical isomers, in particular a pinocembrin racemate, comprising the following steps: (1) derivatizing the mixture of pinocembrin optical isomers to be separated to form a mixture of diastereoisomer derivatives by using a chiral primary amine or a chiral sulfinamide in an organic solvent; (2) separating the diastereoisomer derivatives and dederivatizing the separated isomers to obtain (R)-(+)-pinocembrin and (S)-(−)-pinocembrin with optical activity.

The present invention is suitable for various mixtures of pinocembrin optical isomers which needs to be resolved into (R)-pinocembrin and (S)-pinocembrin, in which (R)-pinocembrin and (S)-pinocembrin exist in any ratio. In one embodiment, the mixture of pinocembrin optical isomers is a racemic pinocembrin.

In the present invention, pinocembrin may be directly derivatized by using a chiral primary amine or chiral sulfinamide to achieve resolution without any pre-treatment. Alternatively, the phenol hydroxyl group of pinocembrin can be optionally protected with a protective group before the derivation of using the chiral primary amine or chiral sulfonamide, and the protective group can be removed after the derivation reaction or the resolution of isomers in R-form and S-form.

In one embodiment, therefore, the phenol hydroxyl group of pinocembrin to be resolved is protected. The protective group can be benzyl, methyl, acetyl, methoxymethyl and the like, as well as other groups suitable for protecting phenol hydroxyl group known to those skilled in the art. As for these protective groups and methods for protection and deprotection, reference can be made to, for example, Greene Woods, *Protective Groups in Organic Synthesis*, Publishing House of East China University of Science and Technology, Shanghai, 2004. In one embodiment of this respect, the protective group is a benzylation agent. Preferably, the benzylation agent is benzyl chloride or benzyl bromide. More preferably, the benzylation agent is benzyl chloride. The reaction for protection of phenol hydroxyl group of pinocembrin may be performed at any suitable temperature. Preferably, the reaction temperature is from 0° C. to 150° C., and more preferably from 60° C. to 80° C. Optionally, the protection reaction is performed in the presence of a base. The base can be selected from sodium carbonate, sodium bicarbonate, potassium carbonate, potassium iodide (see also the protection of phenol hydroxyl group in Example 1), ammonium carbonate and the like. The amount of the base can be determined readily by those skilled in the art according to conventional technical means.

The term "chiral primary amine" used in the present invention refers to a primary levo- or dextro-amine with optical activity, featured with one or more chiral centers in its molecule. Representative structure formula thereof is as follows:

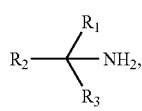

wherein, $R_1$ can be selected from —H, —$CH_3$, —$CH_2CH_3$, —$CH_2CH_2CH_3$, —$CH(CH_3)_2$ and —$CH_2OH$;

$R_2$ can be selected from phenyl, benzyl as well as phenyl and benzyl with other substituents on aromatic ring thereof, —$CH_2OH$, —$CH(OH)CH_3$, —$CH(OH)C_2H_5$ and phCH(OH)—, wherein the substituents can be selected from —$CH_3$, —$CH_2CH_3$, —$CH_2CH_2CH_3$, —$(CH_2)_3CH_3$, —$CH(CH_3)_2$, —$NO_2$, —$CF_3$, —F, —Cl, —I, —OH, —$OCH_3$, —$OC_2H_5$, —$COOCH_3$, —$COOC_2H_5$, —$CONH_2$, —$CONHCH_3$, —$CONHC_2H_5$, —$CON(CH_3)_2$ and —$CONHCH(CH_3)_2$;

$R_3$ has the same definition as those of $R_1$ and $R_2$ with the proviso that $R_3$ does not have the same structure as $R_1$ or $R_2$ does at the same time.

Preferable chiral primary amine is selected from the group consisting of 1-(phenyl)ethylamine, 1-(phenyl)propylamine, 2-(phenyl)propylamine, 2-amino-1-(phenyl)-1,3-propanediol, 2-amino-1-(4-chlorophenyl)-1,3-propanediol and 2-amino-1-(4-nitrophenyl)-1,3-propanediol.

Among the above chiral primary amines, D- or L-α-phenylethylamine is preferred.

The carbonyl group of pinocembrin can be derivatized using the above chiral primary amines to form optical isomer derivatives of pinocembrin with at least two chiral centers. The chiral primary amines are commercially available or can be obtained by synthesis using various methods known in the art.

The "chiral sulfinamide" used in the present invention can be of any chiral forms, featured with one or more chiral centers in its molecule. The structure thereof is as follows:

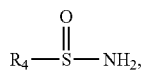

wherein, $R_4$ can be an alkyl having 1-6 carbon atoms, an aryl or aralkyl having 6-9 carbon atoms, a substituted alkyl having 1-6 carbon atoms, a substituted aryl or aralkyl having 6-9 carbon atoms, wherein the substituent can be selected from —$NO_2$, —$CF_3$, —F, —Cl, —I, —OH, —$OCH_3$, —$OC_2H_5$, —$COOCH_3$, —$COOC_2H_5$, —$CONH_2$, —$CONHCH_3$, —$CONHC_2H_5$, —$CON(CH_3)_2$ or —$CONHCH(CH_3)_2$.

Preferable chiral sulfinamide is selected from the following sulfinamides: phenylsulfinamide, p-tolylsulfinamide or tert-butylsulfinamide in R- or S-form.

The carbonyl group of pinocembrin can be derivatized using the above chiral sulfonamides to form optical isomer derivatives of pinocembrin comprising at least two chiral centers The chiral primary amines or chiral sulfonamides used in the present invention preferably are of optically pure.

In the resolution method of the present invention, the chiral primary amine or chiral sulfonamide can be used in any suitable ratio to the pinocembrin mixture especially pinocembrin racemate to be resolved. Preferably, the molar ratio of the chiral primary amine or chiral sulfonamide to the pinocembrin mixture to be separated is 10:1 to 1:1, more preferably 1:1.

The derivation reaction of the mixture of pinocembrin optical isomers with chiral primary amine or chiral sulfonamide according to the present invention can be performed in any suitable organic solvent. The organic solvent can be selected from but not limited to the group consisting of methanol, ethanol, isopropyl alcohol, ethyl acetate, acetone, dichloromethane, chloroform, petroleum ether, ethyl ether, benzene, toluene, DMF, THF and any combination thereof.

In the present invention, the derivation reaction of a mixture of pinocembrin optical isomers with the chiral primary amine or chiral sulfonamide can otherwise be performed under the catalysis of an acid, preferably a Lewis acid. Preferable Lewis acid is $TiCl_4$ or $Ti(OEt)_4$ or a combination thereof. In the derivation reaction, the Lewis acid can be used in any suitable ratio to the mixture of pinocembrin optical isomers. Preferably, the molar ratio thereof is 5:1 to 0.1:1, preferably 0.5:1. Those skilled in the art are familiar with the solvent types which can be used in the derivation reaction.

In one preferable embodiment of the present invention, when the reaction of step (1) is performed, a racemic pinocembrin protected with benzyl group, a chiral primary amine or chiral sulfonamide and triethylamine as well as $TiCl_4$ are added in order. The reaction can be performed at 0° C. and then at room temperature under stirring.

After the end of derivation reaction, the reactant is optionally filtered with Celite and the filter cake is washed sufficiently.

Once the derivation reaction is finished, the product of the derivation reaction can be separated and purified through various suitable methods. Said methods can be chromatography, crystallization or extraction, etc. In one preferable embodiment, the product of the derivation reaction is separated through chromatography, especially column chromatography. The chromatography may separate the diastereomer derivatives of pinocembrin by utilizing their different polarity to obtain a less polar single isomer and a more polar single isomer.

Further, the pinocembrin optical isomer derivatives obtained in step (2) is dederivatized by using a suitable method.

In one embodiment, the dederivation can be achieved by a hydrolization reaction. The hydrolization reaction can be performed in an organic solvent. The organic solvent can be selected from but not limited to the group consisting of methanol, ethanol, isopropyl alcohol, ethyl acetate, acetone, dichloromethane, chloroform, petroleum ether, ethyl ether, benzene, toluene, DMF, THF and any combinations thereof. The hydrolization reaction may also be performed in the presence of an acid. The acid can be selected from an inorganic acid such as HCl, $HNO_3$, $H_2SO_4$, $H_3PO_4$, HOAc or any combinations thereof, or an organic acid such as formic acid, acetic acid, propanoic acid, benzenesulfonic acid, benzoic acid, oxalic acid, chloroacetic acid, trichloroacetic acid, trifluroacetic acid or any combinations thereof. These acids may have any suitable concentrations, for example, a concentration of 1% to 20%, 5% to 15% or 7% to 13%. Preferably, the acid is HCl aqueous solution of a concentration of 10% in the hydrolization system.

If a mixture of pinocembrin optical isomers to be resolved is protected prior to the resolution, the above protected pinocembrin optical isomers can be optionally deprotected after the dederivation is finished. As described above, those skilled in the art know well the protection method of the protected phenolic hydroxyl group, which can be performed by, for example, comprising a reduction reaction. In one embodiment, the reduction reaction is performed by a hydrolysis reaction to achieve the deprotection of phenolic hydroxyl group. The hydrogenation reaction can be performed using Pd/C as catalyst.

Preferably, the molar ratio of Pd/C to the protected pinocembrin is in the range of 0.1:1 to 5:1, more preferably 0.8:1.

After the mixture of pinocembrin optical isomers is subjected to the resolution, the above dederivation and optionally the deprotection, the product can be optionally purified, if desired. The method for purification is similar to those for separating and purifying the derivation reaction product of the step (1), including, for example, column chromatography or recrystallization and the like.

According to one preferred embodiment of the present invention, the reaction scheme thereof is demonstrated as follows:

solvent for the reduction reaction of step (2) is preferably DMF; and the solvent for recrystallization of the reduction product of step (2) is preferably ethanol or an aqueous solution thereof.

The method as provided by the present invention for the resolution of a mixture of pinocembrin optical isomers in particular a pinocembrin racemate is economic and simple, the product has high purity and better yield, so that the method can be used to obtain pinocembrin enantiomers with single configuration in a large scale and may boost further studies and development of pinocembrin optical isomers.

Additionally, the present invention also relates to a (R)-(+)-pinocembrin obtained by the method of resolution according to the present invention.

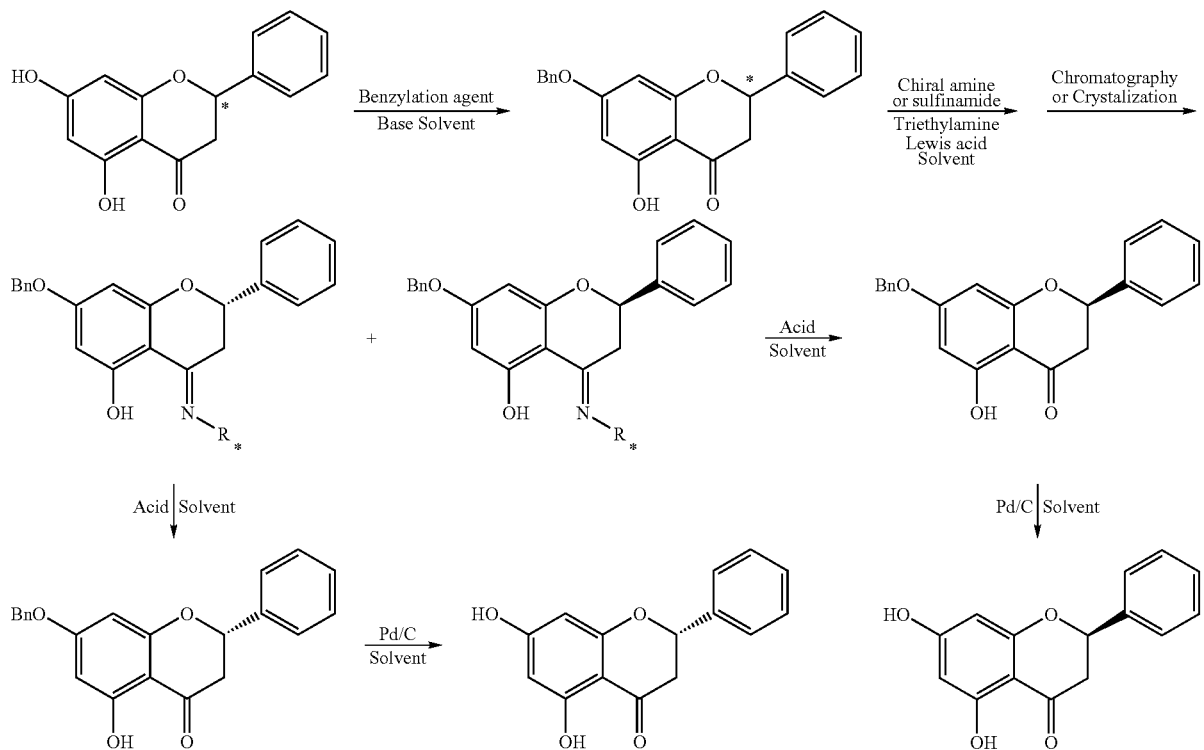

The solvents for reactions, the eluents for column chromatography and the solvents for solidification and recrystallization used in the present invention can be selected from but not be limited to the group consisting of methanol, ethanol, isopropyl alcohol, ethyl acetate, acetone, dichloromethane, chloroform, petroleum ether, ethyl ether, benzene, toluene, DMF, THF, their aqueous solutions with various concentrations, and any combinations thereof. Of which, the solvent for protection reaction of phenolic hydroxyl group is preferably acetone; the solvent for recrystallization is preferably petroleum ether, ethyl acetate or a combination thereof; the solvent for the derivation reaction of step (1) is preferably toluene; the eluent for separating the product of the derivation reaction of step (1) is preferably petroleum ether, ethyl acetate or a combination thereof; the solvent for the hydrolization hydrolysis reaction of step (2) is preferably ethanol, ethyl acetate and a combination thereof, and the recrystallization reaction is preferably ethyl acetate, ethanol or a combination thereof; the The following examples are helpful to understand the present invention, but are not intended to limit the scope of the invention. Throughout the specification, any and all of the publicly available references are incorporated by reference in this patent application. The technicians skilled in the art well understand that any variations, modifications and equivalent replacements of the technical solution of the present invention that do not depart from the spirit and scope of the invention will fall within the scope of the invention.

The e.e. value (enantiomer excess) of pinocembrin in single configuration is measured by high performance liquid chromatography in the Examples, in which the specific parameters are as follows:

Shimadzu LC-10Avp-type high performance liquid chromatography; CLASS-VP chromatography data system; Chiralcel AD-RH column, 5 μm, 150 mm×4.6 mm ID; mobile phase: methanol; flow rate: 0.5 mL/min; column temperature: 20° C.; detection wavelength: 290 nm.

EXAMPLES

Example 1

Protection of Pinocembrin Phenolic Hydroxyl Group

To 100 ml acetone, 8.53 g (33 mmol) of a racemic pinocembrin powder (obtained according to the method of DUAN Yabo et al, *Chinese Journal of Medicinal Chemistry*, 16(6):342-346, 2006) was added, stirred and dissolved, then 5 g (36 mmol) of $K_2CO_3$ powder and 0.31 g (1.88 mmol) of KI were added thereto, stirred for 5 minutes. 5 ml (43 mmol) of benzyl chloride was added, heated with an oil bath to reflux and monitored by TLC until the completion of the reaction (about 4 h). Then stopped heating, cooled to room temperature, inorganic salts were removed by filtration under a reduced pressure, the filter cake was washed fully with acetone, then the filtrate was collected, concentrated, and purified by a common silica gel column chromatography to give a pale yellow oil product, which was solidified with light petroleum to give a solid of benzyl protected racemic pinocembrin (10.26 g, yield 89.0%).

Example 2

Derivatization Reaction and Resolution

To 100 ml toluene, 19.7 g (57 mmol) of the benzyl protected racemic pinocembrin was added, stirred and then cooled to 0° C. with an ice bath. 15 ml (109 mmol) of triethylamine and 7.3 ml (57 mmol) of L-α-methylbenzylamine were dissolved in 20 ml of toluene, and the obtained mixture solution was added to the above reaction liquid, and stirred for 5 minutes. 3.25 ml (29 mmol) of $TiCl_4$ was dissolved in 10 ml of toluene, and the obtained mixture solution was added dropwise to the reaction liquid. After 10 minutes of agitation, the ice bath was removed, and agitation was continued at room temperature. The reaction was subjected to a desiccation treatment, i.e., all instruments and reagents were dried and a $N_2$ protection was used during the reaction. The reaction was monitored by TLC until completion (about 48 h). Stopped agitating, the reaction mixture was filtered through a funnel filled with enough Celite, the filter cake was washed fully with ethyl acetate, the filtrate was collected, concentrated and purified by a common silica gel column chromatography to give a less polar yellow oil product of 6.7 g and a more polar yellow oil product of 7.5 g (total yield was about 55.5%).

Example 3

Dederivation of Resolution Product 7.5 g of the more polar yellow oil product obtained in Example 2 was dissolved in 70 ml of a mixture solvent of ethyl acetate and ethanol in a ratio of 5:2 (V:V), stirred and heated to reflux with an oil bath, and 20 ml of 10% aqueous HCl was added in four batches (each 5 ml) with a time interval of 0.5 h for each batch. The reaction was monitored by TLC until completion (about 2.5 h). Then stopped heating, cooled to room temperature, the reaction mixture was extracted with ethyl acetate and water. The organic phase was collected, concentrated and recrystallized with 95% ethanol to give a white solid of benzyl protected pinocembrin in S-configuration (4.4 g) with specific rotation $[\alpha]_D^{20}=-30.78°$ (c=0.510, acetone).

Example 4

Dederivation of Resolution Product 6.7 g of the less polar yellow oil product obtained in Example 2 was dissolved in 70 ml of a mixture solution of ethyl acetate and ethanol in a ratio of 5:2 (V:V), stirred and heated to reflux with an oil bath, and 20 ml of 10% aqueous HCl was added in four batches (each 5 ml) with a time interval of 0.5 h for each batch. The reaction was monitored by TLC until completion (about 2.5 h). Then stopped heating, the reaction mixture was cooled to room temperature and extracted with ethyl acetate and water. The organic phase was collected, concentrated and recrystallized with 95% ethanol to give a white solid of benzyl protected pinocembrin in R-configuration (4.8 g) with specific rotation $[\alpha]_D^{20}=+30.88°$ (c=0.510, acetone).

Example 5

Deprotection of Dederivation Product 4.4 g of the benzyl protected pinocembrin in R-configuration obtained in Example 3 was dissolved in 100 ml of DMF, 20 ml of 10% aqueous HCl and 3.5 g of 10% Pd—C with a water content of 62.9% were added, and then a hydrogenation at normal pressure was performed. The reaction was monitored by TLC until completion (about 5 h). Then stopped stirring, the reaction mixture was filtered and extracted with ethyl acetate and water. The organic phase was collected, evaporated to remove solvent, and recrystallized with 95% ethanol to give a white solid of (S)-pinocembrin (3.0 g, yield 92%) with specific rotation $[\alpha]_D^{20}=-45.63°$ (c=0.515, methanol), and e.e %>99.3%.

Example 6

Deprotection of Dederivation Product 4.8 g of the benzyl protected pinocembrin in R-configuration obtained in Example 4 was dissolved in 100 ml of DMF, 20 ml of 10% aqueous HCl and 3.5 g of 10% Pd—C with a water content of 62.9% were added, and then a hydrogenation at normal pressure was performed. The reaction was monitored by TLC until completion (about 5 h). Then stop stirring, the reaction mixture was filtered and extracted with ethyl acetate and water. The organic phase was collected, evaporated to remove solvent and recrystallized with 95% ethanol to give a white solid of (R)-pinocembrin (3.1 g, yield 90%) with specific rotation $[\alpha]_D^{20}=+45.83°$ (c=0.515, methanol), and e.e %>99.3%.

Through the method of the present invention, (S)-(−)-pinocembrin with specific rotation $[\alpha]_D^{20} \leq 45.63°$ (c=0.515, methanol) and (R)-(+)-pinocembrin with specific rotation $[\alpha]_D^{20} \geq +45.83°$ (c=0.515, methanol) were obtained. The measurement by chiral HPLC indicated that both of the two optical isomers had an optical purity of 99.3% or more.

What is claimed is:

1. A method for resolution of a mixture of pinocembrin optical isomers, in particular a pinocembrin racemate, said method comprising performing the resolution by using a chiral primary amine or a chiral sulfinamide as a resolving agent.

2. The method according to claim 1, wherein said chiral primary amine and said chiral sulfinamide are respectively represented by the following general formulas:

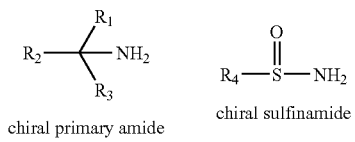

chiral primary amide     chiral sulfinamide wherein, $R_1$ is selected from —H, —$CH_3$, —$CH_2CH_3$, —$CH_2CH_2CH_3$, —$CH(CH_3)_2$ or —$CH_2OH$;

$R_2$ is selected from phenyl, benzyl, or phenyl or benzyl with a substituent on aromatic ring thereof, —$CH_2OH$, —$CH(OH)CH_3$, —$CH(OH)C_2H_5$, phCH(OH)—, wherein the substituent is selected from —$CH_3$, —$CH_2CH_3$, —$CH_2CH_2CH_3$, —$(CH_2)_3CH_3$, —$CH(CH_3)_2$, —$NO_2$, —$CF_3$, —F, —Cl, —I, —OH, —$OCH_3$, —$OC_2H_5$, —$COOCH_3$, —$COOC_2H_5$, —$CONH_2$, —$CONHCH_3$, —$CONHC_2H_5$, —$CON(CH_3)_2$ or —$CONHCH(CH_3)_2$;

$R_3$ has the same definition as those of $R_1$ and $R_2$ with proviso that $R_3$ does not have the same structure as $R_1$ or $R_2$ dose at the same time;

$R_4$ is selected from an alkyl having 1-6 carbon atoms, an aryl or aralkyl having 6-9 carbon atoms, a substituted alkyl having 1-6 carbon atoms, a substituted aryl or aralkyl having 6-9 carbon atoms, wherein the substituent is selected from —$NO_2$, —$CF_3$, —F, —Cl, —I, —OH, —$OCH_3$, —$OC_2H_5$, —$COOCH_3$, —$COOC_2H_5$, —$CONH_2$, —$CONHCH_3$, —$CONHC_2H_5$, —$CON(CH_3)_2$, —$CONHCH(CH_3)_2$.

3. The method according to claim 1, comprising the following steps:

(1) performing a derivation reaction of a mixture of pinocembrin optical isomers, which is optionally subjected to a phenolic hydroxyl group protection, with a chiral primary amine or a chiral sulfinamide to provide a mixture of diastereoisomers, and performing a separation of the mixture of diastereoisomers and optionally performing a purification; and (2) dederivatizing the separated diastereoisomers, and performing a deprotection if the mixture of pinocembrin optical isomers is subjected to the phenolic hydroxyl group protection, and optionally performing a purification, to obtain (R)-(+)-pinocembrin and/or (S)-(−)-pinocembrin.

4. The method according to claim 3, wherein the phenolic hydroxyl group protection is performed by using a protective group before the derivation reaction in the step (1), and the protective group is removed after the derivation.

5. The method according to claim 4, wherein the protective group is benzyl, methyl, acetyl, methoxymethyl, in particular, the phenolic hydroxyl group protection is performed by using benzyl chloride or benzyl bromide.

6. The method according to claim 3, wherein the derivation reaction is performed under the catalysis of a Lewis acid.

7. The method according to claim 3, wherein the molar ratio of the chiral primary amine or chiral sulfinamide to the mixture of pinocembrin optical isomers is in the range of 10:1 to 1:1, preferably 1:1.

8. The method according to claim 3, wherein the chiral primary amine is D- or L-α-phenethylamine; the chiral sulfinimide is a sulfinimide selected from phenylsulfinamide, p-tolylsulfinamide or tert-butylsulfinamide in R- or S-form.

9. The method according to claim 3, wherein the separation or purification of the step (1) is crystallization, extraction or chromatography, especially column chromatography.

10. The method according to claim 3, wherein the step (2) is performed through hydrolysis of the diastereoisomers, especially in the presence of an acid, wherein the acid is preferably an inorganic acid such as HCl, $HNO_3$, $H_2SO_4$, $H_3PO_4$, HOAc or a combination thereof, especially preferably a HCl aqueous solution having a concentration of 10% in the hydrolization hydrolysis system.

11. The method according to claim 3, wherein the deprotection of the dederivatized diastereoisomers is performed through a reduction reaction, preferably through a hydrogenation reaction using Pd/C as catalyst.

12. The method according to claim 6, wherein the Lewis acid is selected from $TiCl_4$ or $Ti(OEt)_4$ or a mixture thereof, and the molar ratio of the Lewis acid to the mixture of pinocembrin optical isomers is preferably in the range of 5:1 to 0.1:1, more preferably 0.5:1.

13. The method according to claim 11, wherein the molar ratio of the Pd/C to the mixture of pinocembrin diastereoisomers is in the range of 0.1:1 to 5:1, preferably 0.8:1.

* * * * *